United States Patent [19]

Stapp

[11] 4,242,228
[45] Dec. 30, 1980

[54] CATALYSTS FOR CONVERSION OF CONJUGATED DIOLEFINS TO DIACYLOXY OLEFINS

[75] Inventor: Paul R. Stapp, Bartlesville, Okla.

[73] Assignee: Phillips Petroleum Company, Bartlesville, Okla.

[21] Appl. No.: 8,150

[22] Filed: Jan. 31, 1979

Related U.S. Application Data

[62] Division of Ser. No. 827,631, Aug. 25, 1977, Pat. No. 4,180,676.

[51] Int. Cl.$^2$ ............... B01J 31/02; B01J 31/04; B01J 27/08; B01J 27/06
[52] U.S. Cl. ................. 252/429 R; 252/428; 252/441
[58] Field of Search ............. 252/429 R, 426, 428, 252/441; 560/246

[56] References Cited

U.S. PATENT DOCUMENTS

| 2,695,313 | 11/1954 | Toland, Jr. | 562/527 |
|---|---|---|---|
| 2,870,196 | 1/1959 | Barney et al. | 560/190 |
| 2,903,480 | 9/1959 | Toland | 562/411 |
| 2,985,521 | 5/1961 | Herman et al. | 44/68 |
| 3,119,874 | 1/1964 | Paszthory et al. | 260/597 B |
| 3,119,875 | 1/1964 | Steinmetz et al. | 260/597 B |
| 3,368,505 | 2/1968 | Harrison | 110/246 |
| 3,479,395 | 11/1969 | Huguet | 560/246 |
| 3,634,496 | 1/1972 | Kominami et al. | 560/245 |
| 4,026,924 | 5/1977 | Stapp | 560/246 |
| 4,044,041 | 8/1977 | Stapp | 560/246 |

FOREIGN PATENT DOCUMENTS 1368505 9/1974 United Kingdom.

OTHER PUBLICATIONS

Suzuki, Ind. Eng. Chem. Prod. Res. Dev., 10, pp. 179–183 (1971).
Hill, Chem. Rev. 61, pp. 537–562 (1961).

*Primary Examiner*—P. E. Konopka

[57] ABSTRACT

A catalyst comprising a uranium compound, an alkali metal ion, and a halide, is effective to convert conjugated dienes in carboxylic acid media to diacyloxy olefins.

20 Claims, No Drawings

CATALYSTS FOR CONVERSION OF CONJUGATED DIOLEFINS TO DIACYLOXY OLEFINS

This is a divisional application of Ser. No. 827,631 filed Aug. 25, 1977, now U.S. Pat. No. 4,180,676.

FIELD OF THE INVENTION

The invention pertains to the oxidation of conjugated dienes to diacyloxy olefins. In another aspect, the invention pertains to a uranium catalyst system.

BACKGROUND OF THE INVENTION

Conjugated dienes, such as butadiene, present an intriguing possible source of a variety of more valuable chemicals. Conjugated dienes, obtained from various sources such as the conversion of refinery streams obtainable in the modern integrated refinery sometimes termed a petrocomplex, are relatively cheap chemicals. Conversion of such unsaturates potentially could provide routes to many other useful and valuable intermediates and end products. For example, 1,4-butanediol is a valuable intermediate used in the preparation of polybutylene terephthalate, an engineering type plastic.

BRIEF DESCRIPTION OF THE INVENTION

I have discovered that a catalyst system comprising a uranium compound, an alkali metal ion, and a halide, is effective for the conversion of conjugated diolefins to diacyloxy olefins. The resulting diacyloxy olefins are readily converted to the corresponding saturated diols, or tetrahydrofuran or substituted tetrahydrofurans.

DETAILED DESCRIPTION OF THE INVENTION

Conjugated Diolefins

The conjugated diolefin can be either acyclic or cyclic, substituted or unsubstituted, and there does not presently appear to be any limitation on molecular size except convenience and availability.

The acyclic conjugated diolefins, preferably of 4 to 16 carbon atoms per molecule for convenience and availability, correspond to the general formula:

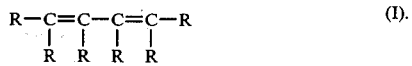

The cyclic conjugated diolefins, preferably of 5 to 16 carbon atoms per molecule for convenience and availability, correspond to the general formula:

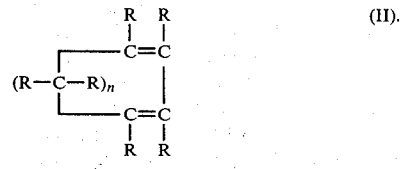

In each of the above formulas, each R is hydrogen, halogen, cyano, —COOR′, or a hydrocarbyl radical of preferably not over 12 carbon atoms, and which can be alkyl, aryl, cycloalkyl, and combinations thereof, such as aralkyl, alkaryl, and the like. R′ is hydrogen, or an alkyl radical of preferably not over 10 carbon atoms, or an aryl radical of preferably not over 10 carbon atoms. The n is an integer, preferably of 1 to 12.

Exemplary linear conjugated diolefins include: 1,3-butadiene, 2-methyl-1,3-butadiene, 2-chloro-1,3-butadiene, 2-ethyl-1,3-butadiene, 2-cyano-1,3-butadiene, 2-methylene-3-butenoic acid, 2,4-pentadienenitrile, 1,3-hexadecadiene, 2-methoxycarbonyl-1,3-butadiene, 2-decyloxycarbonyl-1,3-butadiene, 2-phenoxycarbonyl-1,3-butadiene,2-(1-naphthyloxy)carbonyl-1,3-butadiene, 2-benzyl-1,3-butadiene,2-p-tolyl-1,3-butadiene, 2-chloro-3-methyl-1,3-butadiene, and the like, alone or in admixture; or in admixture with cyclic diolefins; though preferably single species are employed.

Exemplary cyclic conjugated diolefins include 1,3-cyclohexadiene, 1,3-cyclooctadiene, 1,3-cyclododecadiene,5-methyl-1,3-cyclohexadiene, 2,4-cyclohexadiene-1,2-dicarboxylic acid, octafluoro-1,3-cyclohexadiene, hexachlorocyclopentadiene, 5,6,7,8-tetrabromo-1,3-cyclooctadiene, 1,3-cyclohexadecadiene, 2-undecyl-1,3-cyclopentadiene,2-methoxycarbonyl-1,3-cyclooctadiene,2-decyloxycarbonyl-1,3-cyclopentadiene, 2-phenoxycarbonyl-1,3-cyclohexadiene,2-(1-naphthyloxy)carbonyl-1,3-cyclopentadiene, 2-benzyl-1,3-cyclooctadiene, 2-p-tolyl-1,3-cyclohexadiene, and the like, alone or in admixture, though preferably single species are employed.

In a presently preferred embodiment, the conjugated diolefins employed in the process of my invention are the hydrocarbons, those which contain only carbon and hydrogen.

Catalyst System

The catalyst system employed for the conversion of conjugated diolefins in carboxylic acid media to diacyloxy olefins comprises three components: a uranium compound, an alkali metal ion, and a halide, optionally with a dihalobutene. Presently preferably, the catalyst system consists essentially of these components.

A wide range of uranium compounds can be used as the uranium compound component of the instant catalyst system. Such compounds include those derived from complex ions such as the uranyl ion ($UO_2^{2+}$), and the like. Exemplary uranium compounds include uranium dioxide $UO_2$, uranium trioxide $UO_3$; uranium halides such as uranium trichloride $UCl_3$, uranium tetrachloride $UCl_4$, uranium triiodide $UI_3$, uranium tetraiodide $UI_4$, and uranium tribromide $UBr_3$; uranyl halides such as uranium chloride $UO_2Cl_2$, uranyl carboxylates such as uranyl acetate $UO_2(OAc)_2$; uranyl nitrate $UO_2(NO_3)_2$; and the like, alone, or in admixture. The uranium compounds can be employed containing one or more molecules of water of hydration, or in essentially dehydrated form, as may be convenient.

Any alkali metal compound can be used so long as it is suitable and effective, and is sufficiently soluble in the media as to contribute the desired alkali metal ion. The alkali metal can be any one or more of lithium, sodium, potassium, or cesium. Suitable alkali metal compounds include the halides, nitrates, carboxylates, oxides, and hydroxides.

Exemplary alkali metal compounds include lithium chloride, lithium bromide, lithium iodide, lithium acetate, lithium benzoate, lithium oxide, lithium octadecanoate, lithium nitrate, sodium chloride, sodium bromide, sodium acetate, sodium nitrate, potassium chloride, potassium acetate, potassium benzoate, potassium nitrate, rubidium chloride, rubidium bromide, rubidium acetate, rubidium nitrate, cesium chloride, cesium acetate, cesium oxide, cesium nitrate, and the like, and mixtures thereof.

The third component of my catalyst system is a source of halide ion, specifically chloride, bromide, iodide, or mixtures of these ions. The halide ion can be supplied, of course, at least in part, or all, by the uranium compound, by the alkali metal compound, or both. Other halide ion sources can be employed provided that the cation portion of the halide containing compound is substantially inert under the reaction conditions employed according to my invention.

Exemplary halide ion sources include the alkaline earth metal halides, such as magnesium chloride, calcium bromide, magnesium iodide, strontium bromide, barium chloride, and the like, as well as the appropriate already described uranium compounds and alkali metal compounds.

It is optional, though presently preferred, to further employ a dihalobutene, such as 1,4-dichloro-2-butene or the corresponding dibromo or diodo compounds, as a catalyst adjuvant. The dihalobutenes appear to serve as sources of halide ion and to promote the reaction rate of the oxidation reaction.

The amount of my catalyst system employed in the process of my invention can be expressed in terms of the mole percent of the uranium compound based on the amount of the conjugated diolefin charged to the reaction mixture. The ratios can range widely, so long as effective for the oxidation results desired. Presently considered exemplary is an amount of the uranium compound in the range of about 0.1 to 40, preferably about 1 to 20, more preferably about 1 to 10, mole percent of the conjugated diolefin.

The amounts of the alkali metal compound and of the halide ion employed in the process of my invention are based on the uranium compound. The molar ratios can range widely, so long as effective for the oxidation results desired. Presently considered exemplary is a molar ratio of the alkali metal compound to the uranium compound, and a molar ratio of the halide ion to the uranium compound, each in the range of about 0.1:1 to 20:1, preferably about 1:1 to 10:1.

Similarly, when employed, the amount of the dihalobutene catalyst adjuvant is based on the uranium compound. The ratios can range widely, so long as effective for the oxidation results desired. Presently considered exemplary is a molar ratio of the dihalobutene to the uranium compound of about 0.1:1 to 10:1, preferably about 0.5:1 to 5:1.

Carboxylic Acid Media/Reactant

The term carboxylic acid media includes the use of mono- or dicarboxylic acids alone, or in admixture with each other, or with the anhydrides. The carboxylic acid employed in the process of my invention includes monocarboxylic acids, dicarboxylic acids, or both, preferably of up to 18 carbon atoms per molecule for availability and to be reasonably liquid under suggested reaction conditions, and most preferably in conjunction with an anhydride.

The monocarboxylic acids, preferably of 2 to 18 carbon atoms per molecule, can be characterized by the (III) general formula $R'''$—COOH in which $R'''$ is an alkyl, cylcoalkyl, or aryl radical, and includes halogen, cyano, and —COOR' substituted derivatives thereof wherein up to four halogen, cyano, or —COOR' substituents can be present in the $R'''$ group. R' is as previously defined.

The dicarboxylic acid, preferably of 2 to 18 carbon atoms per molecule, can be characterized by the general formula (IV) $R''''(COOH)_2$ in which $R''''$ is a valence bond, or is an alkylene, cycloalkylene, or arylene radical, in which up to four halogen, cyano and —COOR' substituents can be present in the $R''''$ group. R' is as previously defined.

Exemplary carboxylic acids include acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, oxalic acid, succinic acid, adipic acid, terephthalic acid, 2-bromobutanoic acid, ethyl hydrogen adipate, 4-chlorobenzoic acid, 4-cyclohexylbenzoic acid, 2,3,4,5-tetrachlorobenzoic acid, ethyl hydrogen-o-phthalate, 4,6,8,10-tetracyanoundecanoic acid, 4,6,8,10-tetramethoxycarbonylundecanoic acid, 4-decyloxycarbonylcyclohexanecarboxylic acid, tetrabromo-1,4-benzenedicarboxylic acid, tetracyano-1,4-benzenedicarboxylic acid, tetramethoxycarbonyl-1,4-benzenedicarboxylic acid, 2-decyloxycarbonylhexanedioic acid, and the like, alone, or in admixture.

It is optional, though presently preferred, to employ, as part of the reaction mixture, a carboxylic acid anhydride in addition to the carboxylic acid, preferably the corresponding carboxylic acid anhydride. The use of a carboxylic acid anhydride serves to simplify the purification and separation steps by reducing the amount of by-products which contain free hydroxy groups. Exemplary anhydrides include those corresponding to the described acids and need not be individually recited.

The presently preferred carboxylic acid is acetic acid, and presently preferred is a carboxylic acid media of acetic acid/acetic anhydride.

Reaction Conditions

The process of my invention is an oxidation reaction and as such as carried out in the presence of free oxygen. The amount of oxygen present is not believed to be critical, though it is recognized that an undesirably slow reaction will result if the concentration of oxygen is very low. Pure oxygen can be employed, or mixtures of oxygen with inert gases such as air can be employed as a convenient source of free oxygen for my process.

It is recognized that explosive conditions could be attained if the amount of oxygen added to the reaction system is not properly controlled. The process of my invention, as is true with many oxidation reactions, is highly exothermic and this aspect further dictates caution in adding oxygen to the reaction system. Because of these considerations, it is desirable to add the oxygen incrementally or continuously during the reaction to avoid reaching an explosive range of oxygen concentration, and to allow better control of the temperature of the reaction. A reaction vessel with efficient mixing means is thus desirable to avoid build-up of potentially dangerous concentrations of free oxygen.

The reactions of my process can be carried out at any convenient temperature so long as the temperature is effective for the reactions, and not so high as to be unduly hazardous. Exemplary temperatures lie in the range of about 25° C. to 200° C., presently preferably about 70° C. to 150° C.

The process can be carried out under any suitable oxygen pressurization over a broad range, so long as sufficient oxygen is provided to be effective in the oxidation reaction, not cause unduly long times of reaction, and at the same time not be so high in concentration as to provide unduly hazardous conditions. An exemplary range of oxygen pressure is about 0.1 to 1,000, presently preferably about 5 to 200, psig of oxygen above autogenous pressure at the temperature employed.

The reaction time can range widely, as desired or convenient. The reaction time depends on the temperature, catalyst activity, and the oxygen pressure employed. An exemplary range is about 0.1 to 12 hours.

The reaction of my invention is carried out in the contact with carboxylic acid media which provides the acyloxy and/or acyl moiety of the final product. Although some diacyloxy olefin product can be obtained using a wide range of ratios of carboxylic acid media to conjugated diolefin, it presently is apparent that the best yields can be obtained when the molar ratio of carboxylic acid to conjugated diolefin reactant is at least about 2:1. In this connection, one mole of the corresponding carboxylic anhydride is equivalent to 2 moles of carboxylic acid. Ratios lower than about 1:1 should not be employed due to reduced yields, and ratios considerably higher than 2:1 can be employed, such as up to about 50:1 or higher, since the excess carboxylic acid media then serves as a reaction diluent.

The ratio of acid:anhydride, where the anhydride is employed, can range widely so long as effective. A suggested ratio is about 1:2 to 4:1, present preferred about 2:1 by volume.

The process of my invention can be carried out in a batch or a continuous fashion, and in the liquid phase or in the gas phase. In a presently preferred embodiment, the process is carried out in the liquid phase. When conducted in the liquid phase, it is preferred that the carboxylic acid media employed in the process of my invention be normally liquid or at least liquid under the conditions employed for the reaction.

Product Recovery

Reaction mixtures obtained in the process of my invention can be readily treated for product recovery. The reaction mixture generally is vented to remove any unreacted oxygen and conjugated diolefin, and then distilled to remove remaining carboxylic acid media. The product remaining then can be treated, such as by distillation, to recover one or mor fractions containing the desired diacyloxy olefin product. In many instances the catalyst can be recovered from the distillation residue, such as by evaporation of the residue to dryness, and recycled to the reaction zone as desired.

The diacyloxy olefins recovered from the product mixture include in many instances an amount of 1,2- or vicinal isomer which can be recycled to the reaction zone and thereby converted to the more desired 1,4-diacyloxy olefin. Of course, unreacted conjugated diolefin also can be recycled if desired.

Diacyloxy Olefins

Diacyloxy olefins produced according to the process of my invention can be represented by the following general formulas using reactants as indicated:

| Reactants | | Products |
|---|---|---|
| Carboxylic Acid Formula | Conjugated Diolefin Formula | Diacyloxy Olefin |
| (IV) | (I) | ![structure V] |
| (IV) | (II) | ![structure VI] |
| (V) | (I) | ![structure VII] |
| (V) | (II) | ![structure VIII] |

The product formulas V, VI, VII, and VIII depict only the predominant diacyloxy olefin product obtained in the reactions indicated. These products generally are accompanied by relatively smaller amounts of isomeric diacyloxy olefins. For example, using general formula VII as an illustration, the isomeric product can be represented by the general formula:

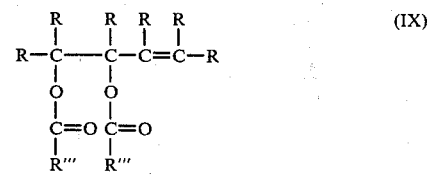
(IX)

Examples of diacyloxy olefins of product formula V include: 1,4-diacetoxy-2-butene, 1,4-diacetoxy-2-hexadecene, 1,4-dioctanoyloxy-2-chloro-3-methyl-2-butene, 1,4-di(trichloroacetoxy)-2-cyano-2-butene, and 1,4-dibenzoyloxy-2-ethoxycarbonyl-2-butene.

Examples of diacyloxy olefins of product formula VI include: 3,5-diacetoxycyclopentene, 3,6-di(chloroacetoxy)cyclohexene, 3,8-di(cyanoacetoxy)cyclooctene, 3,12-diacetoxycyclododecene, 3,8- dibutanoyloxy-4,5,6,7-tetrabromocyclooctene and 3,5-di(trichloroacetoxy)hexachlorocyclopentene.

Examples of diacycloxy olefins of product formula VII include: 1,4-butene-2-diyl di(hydrogen oxalate), 1,4-butene-2-diyl di(hydrogen adipate), 2-chloro-3-methyl-1,4-butene-2-diyl di(hydrogen succinate), and 1,4-hexadecene-2-diyl di(hydrogen terephthalate).

Examples of diacyloxy olefins of product formula VIII include: 3,5-cyclopentenediyl di(hydrogen oxalate), 3,8-cyclooctenediyl di(hydrogen succinate), 3,6-cyclohexenediyl di(hydrogen adipate) and 3,12-cyclododecenediyl di(hydrogen terephthalate).

EXAMPLES

The following examples are intended to assist one skilled in the art to an understanding of the invention. Particular species, amounts, and relationships are intended to be exemplary and not limitative of the scope of my invention.

EXAMPLE I

In a run carried out according to my invention, a 250 ml Fisher-Porter aerosol compatibility bottle equipped with a magnetic stirrer was charged with 4.5 grams (10 mmoles) of uranyl acetate dihydrate, 2.3 grams (10.7 mmoles) of 1,4-dibromo-2-butene, 6.5 grams (75 mmoles) of lithium bromide, 50 ml of acetic acid, 25 ml of acetic anhydride, and 11.4 grams (210.7 mmoles) of 1,3-butadiene in the vapor phase. The bottle reactor was placed in an oil bath, pressured to 30 psig with oxygen and heated to 140° C. About 1 hour was required to reach the desired reaction temperature after which the reaction was continued for 6 hours. During the reaction the reactor was repressured to 130 psig with oxygen at about 20-30 minute intervals. At the end of the reaction the bottle reactor was cooled, vented, and weighed. A weight gain of 5.4 grams was obtained during the oxidation reaction.

The reaction mixture was transferred to a distillation flask and distilled through an 18" Vigreaux column. Two fractions were collected during the distillation. Fraction 1 boiling over a range of 42-50° C. at 50 mm mercury pressure weighed 104.8 grams, and fraction 2 boiling from 71-110° C. at 5 mm mercury pressure weighed 18.4 grams. Based on previous experience in similar oxidation reaction runs, fraction 1 consisted essentially of acetic acid and acetic anhydride.

Fraction 2 was analyzed by gas-liquid phase chromatography which indicated the presence of 2.83 grams (16.5 mmoles) of 1,2-diacetoxy-3-butene, 2.03 grams (11.8 mmoles) of cis-1,4-diacetoxy-2-butene and 9.14 grams (53.1 mmoles) of trans-1,4-diacetoxy-2-butene. The yield of diacetoxy butenes based on the 1,3-butadiene charged was thus 38.6%.

The results of this run demonstrate the effectiveness of my catalyst system for the oxidation of conjugated dienes to diacyloxy butenes in carboxylic acid media.

EXAMPLE II

Another run was carried out utilizing the same type of apparatus and procedure as described in Example I above. In this run, the reactor was charged with 3.7 grams (10 mmoles) of thorium tetrachloride, 2.3 grams (10.7 mmoles) of 1,4-dibromo-2-butene, 6.5 grams (75 mmoles) of lithium bromide, 50 ml of acetic acid, 25 ml of acetic anhydride, and 12.5 grams (231.1 mmoles) of 1,3-butadiene charged in the vapor phase. The reactor was placed in an oil bath, pressured to 30 psig with oxygen, and heated to 140° C. About 1.5 hours was required to reach the desired reaction temperature after which the reaction was continued for 6.3 hours. During the reaction the reactor was repressured to 120 psig with oxygen at about 20-30 minute intervals. At the end of the reaction the reactor was cooled, vented, and opened. It was observed that the reaction mixture had become a viscous black material.

The reaction mixture was treated with a mixture of diethyl ether and water. The diethyl ether layer was separated, washed with water, neutralized with sodium carbonate solution, and dried over anhydrous magnesium sulfate. The diethyl ether extract was filtered and the ether then removed on a rotary evaporator. The residue remaining was a dark oily material which weighed 18.2 grams. This material was analyzed as in Example I by gas-liquid phase chromatography. The analysis indicated the presence of 1.88 grams (10.9 mmoles) of 1,2-diacetoxy-3-butene, 0.73 grams (4.2 mmoles) of cis-1,4-diacetoxy-2-butene and 3.48 grams (20.3 mmoles) of trans-1,4-diacetoxy-2-butene. The yield of diacetoxy butenes based on the 1,3-butadiene charged to the reaction was only 15.3%.

The results of this control run demonstrate that the use of a heavy metal catalyst component though very close to uranium in atomic number was not suitable for the production of good yields of diacetoxy butenes from the oxidation of conjugated dienes to diacyloxy olefins in carboxylic acid media.

Conversion of Diacyloxy Olefins to Diols

The diacyloxy olefins can be converted to diols by several known methods. For example, the diacyloxy olefins can be hydrolyzed under basic or acidic conditions to give the olefinic diols which then can be hydrogenated to remove the olefinic unsaturation and thus provide other diols. Alternatively, the diacyloxy olefins can be hydrogenated first to remove olefinic unsaturation and then hydrolyzed to provide diols.

Utility

The diols are useful for conversion to polyesters or polyurethanes, and as solvents or humectants, or can be converted to the corresponding tetrahydrofuran or substituted tetrahydrofurans. Tetrahydrofuran itself has wide utility as a solvent, and as a randomizing agent in preparation of copolymers. The substituted tetrahydrofurans are useful for solvents and intermediates in the preparation of diamines or dicarboxylic acids for polyamide preparation.

The disclosure, including data, has illustrated the value and effectiveness of my invention. The examples, the knowledge and background of the field of the invention and of general principles of chemistry and other applicable sciences, have formed the bases to which the broad descriptions of the invention, including the ranges of conditions and generic groups of operant components have been developed, and have formed the bases for my claims here appended.

I claim:

1. The composition consisting essentially of catalytically effective ratios to convert conjugated dienes to diacyloxy olefins of (A) a uranium compound, (B) an alkali metal ion, (C) a halide which is chloride, bromide, or iodide, and at least one of (D) a dihalobutene and (E) carboxylic acid media; wherein said (C) halide is supplied from the group consisting of said (A) uranium compound, an alkali metal compound supplying said (B) alkali metal ion, and alkaline earth metal halides.

2. The composition according to claim 1 wherein said (A) uranium compound is a uranium or uranyl halide, oxide, nitrate, or carboxylate.

3. The composition according to claim 2 wherein said (A) uranium compounds isuranium dioxide, uranium trioxide, uranium trichloride, uranium tribromide, uranium tetraiodide, uranium triiodide, uranyl chloride, uranyl acetate, uranyl nitrate, or mixture thereof.

4. The composition according to claim 1 wherein said (B) alkali metal ion is supplied by an alkali metal compound which is lithium chloride, lithium bromide, lithium iodide, lithium acetate, lithium benzoate, lithium oxide, lithium octadecanoate, lithium nitrate, sodium chloride, sodium bromide, sodium acetate, sodium nitrate, potassium chloride, potassium acetate, potassium benzoate, potassium nitrate, rubidium chloride, rubidium bromide, rubidium acetate, rubidium nitrate, cesium chloride, cesium acetate, cesium oxide, cesium nitrate, or mixture thereof.

5. The composition of claim 1 employing a mole ratio of alkali metal compound to provide said (B) alkali metal ion and of said (C) halide each in the range of about 0.1 to 20 moles per mole of said (A) uranium compound; and of said (D) dihalobutene where employed in the molar ratio range of about 0.1:1 to 10:1 relative to said (A) uranium compound.

6. The composition of claim 5 employing a mole ratio of alkali metal compound and of said (C) halide each in the range of about 1 to 10 moles per mole of said (A) uranium compound; and of said (D) dihalobutene where employed in the molar ratio range of about 1:1 to 10:1 relative to said (A) uranium compound.

7. The composition of claim 1 wherein said (C) halide is substantially supplied by compounds providing said (B) alkali metal ion, said (A) uranium compound, or both.

8. The composition of claim 1 wherein said (C) halide is at least in part provided by at least one of an alkali metal halide or alkaline earth metal halide.

9. The composition of claim 5 consisting essentially of said (A), (B), (C), and (D).

10. The composition of claim 9 wherein said (A) is uranyl diacetate, said (B) is lithium bromide, said (C) is at least one of bromide and chloride, and said (D) is 1,4-dibromo-2-butene.

11. The composition of claim 1 including said (E) carboxylic acid media.

12. The composition of claim 11 wherein said (E) carboxylic acid media is at least one monocarboxylic acid, dicarboxylic acid, or an anhydride thereof.

13. The composition of claim 12 wherein said (E) carboxylic acid media is at least one mono- or dicarboxylic aliphatic or aromatic acids, or anhydride, of 2 to 18 carbon atoms per molecule.

14. The composition of claim 13 wherein said (E) carboxylic acid media monocarboxlic acid is represented by the formula R'''—COOH, and said dicarboxylic acid dicarboxylic acid is represented by the formula R''''(COOH)$_2$;

wherein R''' is selected from the group consisting of alkyl, cycloalkyl, and aryl radicals, and halogen, cyano, and —COOR' substituted derivatives thereof wherein up to four of said halogen, cyano or —COOR' substituents can be present in said R''' radical, and R'''' is selected from the group consisting of a valence bond and alkylene, cycloalkylene and arylene radicals, and halogen, cyano and —COOR' substituted derivatives thereof wherein up to four of said halogen, cyano or —COOR' substituents can be present in said wherein R'''' radical; and R' is selected from the group consisting of hydrogen, an alkyl radical of up to 10 carbon atoms, and an aryl radical of up to 10 carbon atoms.

15. The composition of claim 14 wherein said (E) carboxylic acid media comprises said monocarboxylic acid selected from the group consisting of acetic acid, propanoic acid, butanoic acid, pentanoic acid, hexanoic acid, octanoic acid, dodecanoic acid, octadecanoic acid, cylopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, 2-bromobutanoic acid, ethyl hydrogen adipate, 4-chlorobenzoic acid, 4-cyclohexylbenzoic acid, 2,3,4,5-tetrachlorobenzoic acid, ethyl hydrogen-o-phthalate, 4,6,8,10-tetracyanoundecanoic acid, 4,6,8,10-tetramethoxycarbonylundecanoic acid, 4-decyloxycarbonylcyclohexanecarboxylic acid, their anhydrides, and mixtures thereof.

16. The composition of claim 14 wherein said carboxylic acid media comprises said dicarboxylic acid selected from the group consisting of oxalic acid, succinic acid, terephthalic acid, adipic acid, tetrabromo-1,4-benzenedicarboxylic acid, tetracyano-1,4-benzenedicarboxylic acid, tetramethoxycarbonyl-1,4-benzenedicarboxylic acid, 2-decyloxycarbonylhexanedioic acid, their anhydrides, and mixtures thereof.

17. The composition of claim 11 consisting essentially of said (A), (B), (C), and (E).

18. The composition of claim 17 wherein said (A) is uranyl diacetate, said (B) is lithium bromide, said (C) is at least one of bromide and chloride, said (E) is at least one of acetic acid and acetic anhydride.

19. The composition of claim 11 consisting essentially of said (A), (B), (C), (D), and (E).

20. The composition of claim 19 wherein said (A) is a uranyl diacetate, said (B) is lithium bromide, said (C) is at least one of chloride and bromide, said (D) is 1,4-dibromo-2-butene, and said (E) is at least one of acetic acid and acetic anhydride.

* * * * *